United States Patent [19]
Jackson

[11] Patent Number: 6,040,333
[45] Date of Patent: *Mar. 21, 2000

[54] DIETARY SUPPLEMENTS

[75] Inventor: Sherry D. Jackson, New York, N.Y.

[73] Assignee: Energetics, Inc., New York, N.Y.

[ * ] Notice: This patent is subject to a terminal disclaimer.

[21] Appl. No.: 08/873,792

[22] Filed: Jun. 12, 1997

Related U.S. Application Data

[63] Continuation-in-part of application No. 08/688,448, Jul. 30, 1996, Pat. No. 5,654,011.

[51] Int. Cl.$^7$ .......................... A61K 31/35; A61K 35/78

[52] U.S. Cl. .................... 514/456; 514/874; 514/899; 424/195.1

[58] Field of Search .................... 424/195.1; 514/182, 514/455, 456, 874, 899

[56] References Cited

U.S. PATENT DOCUMENTS

| | | | |
|---|---|---|---|
| 3,864,362 | 2/1975 | Feuer et al. | 549/403 |
| 4,826,831 | 5/1989 | Plunkett et al. | 514/170 |
| 5,424,331 | 6/1995 | Shlyankevich | 514/456 |
| 5,431,925 | 7/1995 | Ohmori et al. | 424/646 |
| 5,498,631 | 3/1996 | Gorbach et al. | 514/456 |
| 5,506,211 | 4/1996 | Barnes et al. | 514/27 |
| 5,514,382 | 5/1996 | Sultenfuss | 424/440 |
| 5,516,528 | 5/1996 | Hughes et al. | 424/464 |
| 5,523,087 | 6/1996 | Shlyankevich | 424/195.1 |
| 5,565,199 | 10/1996 | Page et al. | 424/195.1 |
| 5,569,459 | 10/1996 | Shlyankevich | 424/195.1 |

FOREIGN PATENT DOCUMENTS

WO 93/23069  11/1993  WIPO.

OTHER PUBLICATIONS

Hendler, Sheldon S., The Complete Guide to Anti–Aging Nutrients, 1985, Simon and Schuster, NY pp. 293–321.
Adlercreutz, et al., *Urinary Excretion of Lignans* . . . , Am J Clin Nutr, vol. 54, pp. 1093–1100, 1991.
Murkies, et al., *Dietary Flour Supplementation Decreases Post–Menopausal* . . . , Am J Clin Nutr, vol. 55, pp. 131–138, 1992.
Selhub, et al., *The Pathogenesis of Homocysteinemia:* . . . , Am J Clin Nutr, vol. 55, pp. 131–138, 1992.
Czeizel, et al., *Prevention of The First Occurrence* . . . , The New England Journal of Medicine, vol. 327, No. 26, pp. 1832–1835, 1992.
Butterworth, et al., *Folic Acid Safety and Toxicity:* . . . , Am J Clin Nutr, vol. 50, pp. 353–358, 1989.
Bailey, Ph.D., L.B., *Evaluation of A New Recommended Dietary Allowance for Folate*, J Amer Dietetic Assn, vol. 92, pp. 463–468, 1992.
Butterworth, et al., *Improvement in Cervical Dysplasia* . . . , The Amer Jour of Clin Nutr, vol. 35, pp. 73–82, 1982.
Genest, Jr., et al., *Plasma Homocystine Levels in Men* . . . , J Amer Coll of Cardiol, vol. 16, pp. 1114–1119, 1990.
Brattstrom, et al., *Folic Acid—An Innocuous Means to Reduce Plasma Homocysteine*, Scand J Clin Lab Invest, vol. 48, pp. 215–221, 1988.
Ueland, et al., *Plasma Homocysteine, A Risk Factor For Vascular Disease:* . . . ,J Lab Clin Med, vol. 114, No. 5, pp. 473–501, 1989.
Stampfer, et al., *A Prospective Study of Plasma Homocyst(E)ine* . . . , JAMA, vol. 268, pp. 877–881, 1992.
Malone, W.F., *Studies Evaluating Antioxidants and β–Carotene* . . . , Am J Clin Nutr, vol. 53, pp. 305S–313S, 1991.
Manson, et al., *Antioxidant Vitamin Score and Incidence* . . . , Abstracts from the 65th Scientific Sessions, #2687, p. 1–675 (no date available).
Malter, et al., *Natural Killer Cells, Vitamins* . . . , Nutrition and Cancer, vol. 12, pp. 271–178, 1989.
Chandra, et al., *Nutritional Support Improves Antibody Response* . . . , British Medical Journal, vol. 291, pp. 705–706, 1985.
Chandra, R.K., *Effect of Vitamin and Trace–Element Supplementation* . . . , The Lancet, vol. 340, pp, 1124–1127, 1992.
Hathcock, et al., *Micronutrient Safety*, Annals NY Acad Aci, pp. 257–266 (no date).
Parfitt, et al., *Bone Remodeling and Bone Loss:* . . . , Clinical Obstetrics and Gynecology, vol. 30, pp. 789–811, 1987.
Meydani, et al., *Vitamin E Supplementation* . . . , Am J Clin Nutr, vol. 52, pp. 557–563, 1990.
Nielsen, et al., *Effect of Dietary Boron on Mineral* . . . , FASEB J, vol. 1, pp. 394–397, 1987.
Nielsen, F.H., *Studies on The Relationship Between Boron and Magnesium* . . . , Magnesium Trace Elem, vol. 9, pp. 61–69, 1990.
Rivlin, R.S., *An Update on Calcium:* . . . , Am J Clin Nutr, vol. 54, pp. 177–178, 1991.
McCarron, et al., *Dietary Calcium and Blood Pressure:* . . . , Am J Clin Nutr, vol. 54, pp. 215S–219S, 1991.
Garland, et al., *Can Colon Cancer Incidence and Death Rates* . . . , Am J Clin Nutr, vol. 54, pp. 193S–201S, 1991.
Cohen, et al., *Magnesium Malabsorption in Postmenopausal Osteoporosis*, Magnesium, vol. 2, pp. 139–143, 1983.
Cohen, et al., *Bone Magnesium, Crystallinity Index* . . . , Magnesium, vol. 2, pp. 70–75, 1983.
Cohen, et al., *Infrared Spectroscopy and Magnesium* . . . , Israel Journal of Medical Sciences, vol. 17, pp. 1123–1125, 1981.
Abraham, et al., *A Total Dietary Program Emphasizing Magnesium* . . . , The Journal of Reproductive Medicine, vol. 35, pp. 503–507, 1990.
Fatemi, et al., *Effect of Experimental Human Magnesium Depletion* . . . , J of Clin Endocrinology and Metabolism, vol. 73, pp. 1067–1072, 1991.
Morgan, et al., *Magnesium and Calcium Dietary Intakes* . . . , J Amer Coll Nutr, vol. 4, pp. 195–206, 1985.

(List continued on next page.)

*Primary Examiner*—John Pak
*Attorney, Agent, or Firm*—Kenyon & Kenyon

[57] ABSTRACT

The present invention relates to dietary supplements containing low doses of phytoestrogens for supplementing the specific phytochemical dietary needs of perimenopausal and menopausal women.

6 Claims, No Drawings

OTHER PUBLICATIONS

Reginster, et al., *Preliminary Report of Decreased Serum Magnesium* . . . , Magnesium, vol. 8, pp. 106–109, 1989.

Anderson, *Chromium Metabolism and Its Role in Disease Processes in Man*, Clin Physiol Biochem, vol. 4, pp. 31–42, 1986.

Lee, et al., *Beneficial Effect of Chromium Supplementation on Serum Triglyceride Levels in NIDDM*, Diabetes Care, vol. 17, No. 12, pp. 1449–1452, 1994.

Abraham, et al., *The Effects of Chromium Supplementation of Serum Glucose* . . . , Metabolism, vol. 41, No. 7, pp. 768–771, 1992.

Mossop, *Trivalent Chromium, In Atherosclerosis and Diabetes*, Central African Journal of Medicine, vol. 37, No. 11, pp. 369–374, 1991.

Simonoff, *Chromium Deficiency and Cardiovascular Risk*, Cardiovascular Research, vol. 18, pp. 591–596, 1984.

Doll, et al., *Pyridoxine (viatmin $B_6$) and The Premenstrual Syndrome: A Randomized Crossover Trial*, Journal of the Royal College of General Practitioners, vol. 39, pp. 364–368, 1989.

Gunn, *Vitamin $B_6$ and The Premenstrual Syndrome (PMS)*, University Health Service, Reading, Berkshire, UK, pp. 213–224, 1985.

Stewart, *Clinical and Biochemical Effects of Nutritional* . . . , The J of Reproductive Med, vol. 32, No. 6, pp. 435–441, 1987.

Kendall, et al., *The Effects of Vitamin B6 Supplementation on Premenstrual Symptoms*, Obstetrics and Gynecology, vol. 70, No. 2, pp. 145–149, 1987.

Havens, *Tactics for Intervention*, Premenstrual Syndrome, vol. 77, No. 7, pp. 32–37, 1985.

Brush, et al., *Pyridoxine in the Treatment of Premenstrual Syndrome*, The British Journal of Clinical Practice, vol. 42, No. 11, 1988.

M. Levine, et al., *Vitamin C pharmacokinetics in healthy volunteers: Evidence for a recommended dietary allowance*, Proc. Natl. Acad. Sci. USA, vol. 93, pp. 3704–3709, Apr. 1996.

J.W. Anderson, M.D., et al., *Metal–Analysis of The Effects of Soy Protein Intake on Serum Lipids*, New England Journal of Medicine, vol. 333, No. 5, pp. 276–282, Aug. 3, 1995.

A. Fugh–Berman, M.D., *Phytoestrogens, Botanical Medicine in Modern Clinical Practice*, Columbia College of P&S, Rosenthal Center, May 16, 1996.

N.G. Stephens, et al., *Randomised controlled trial of vitamin E in patients with coronary disease: Cambridge Heart Antioxidant Study (CHAOS)*, The Lancet, vol. 347, pp. 781–786, Mar. 23, 1996.

C. Herman, et al., *Soybean Phytoestrogen Intake and Cancer Risk*, American Institute of Nutrition, pp. 757S–770S, 1995.

M.J. Messina, et al., *Soy Intake and Cancer Risk: A Review of the In Vitro and In Vivo Data*, Nutrition and Cancer 21, pp. 113–134, 1994.

M. Messina, *Isoflavone intakes by Japanese were overestimated*, Am J Clin Nutr, p. 645, 1995.

Breslau, et al., Relationship of Animal Protein–Rich Diet to Kidney Stone Formation and Calcium Metabolism, Journal of Clinical Endocrinology and Metabolism, vol. 66, No. 1, pp. 140–146, 1988.

Adlercruetz, *Western diet and Western disease: some hormonal and biochemical mechanisms and associations*, Scand J Clin Lab Invest, 50, Suppl 201:3–23, 1990.

Bukoski et al., *Calcium–regulating hormones in hypertension: vascular actions* [1-3], Am J Clin Nur, pp. 220–226, 1991.

Lipkin, M., *Application of intermediate biomarkers to studies of cancer prevention in the gastrointestinal tract: introduction and perspective* [1-3], Am J Clin Nur, pp. 188–192, 1991.

Wargovich et al., *Modulating effects of calcium in animal models of colon carcinogenesis and short–term studies in subjects at increased risk for colon cancer* [1-2], Am J Clin Nur, pp. 202–205, 1991.

Carroll et al., *Calcium and carcinogenesis of the mammary gland*[1-3,] Am J Clin Nur, pp. 206–208, 1991.

Newmarket al., *Colonic hyperproliferation induced in rats and mice by nutritional–stress diets containing four components of a human Western–style diet (series 2)* [1-3], Am J Clin Nur, pp. 209–214, 1991.

Centrum® Label, Lederle Consumer Health Division, American Cyanamid Company, Pearl River, NY 10965; 1995.

Centrum Silver® Label, Lederle Consumer Health Division, American Home Products, Madison, NJ 07940; 1996.

One–A–Day Womens's® Label, Bayer Corporation, Elkhart, IN 46515 (No date available).

Centrum® Label 1992, Lederle Consumer Health Division, American Cyanamid Company, Pearl River, NY 10965, (No date available).

One–A–Day Women's Label, Miles Inc., Elkhart, IN 46515 (No date available).

Mindell, E, Vitamin Bible, *Your Special Vitamin Needs*, pp. 195–217, Warner Books, 1991.

Brzezinski et al., *Short–term Effects of Phytoestrogen–rich Diet on Postmenopausal Women*, Journal of The North American Menopause Society, 4:2, 1997.

Herman et al., *Soybean Phytoestrogen Intake and Cancer Risk*, Journal of Nutrition, 125:3S, Mar. 1995 Supplement.

Knight et al., *A Review of the Clinical Effects of Phytoestrogens*, Obstetrics & Gynecology, 87:5, May 1996.

*Soy for Hot Flashes*, News Bites (Date unavailable).

Power–Herbs: Phyto Estrogen–Power Label, Nature's Herbs, American Fork, UT 84003 (Date unavailable.

Fem Change Herbal Formula Label, Nature's Herbs, American Fork, UT 84003 (Date unavailable).

Soy Super Complex: Phyto–Nutrients with High Potency Isoflavonoid Complex Label, Rainbow Light (Date unavailable).

Solgar Supplement—*Genistein from Standardized Soy Isoflavone Extract is Promoted as a Breakthrough Phytonutrient*—Manufacturer is Sogar Vitamin, May 13, 1996.

Genistein: Soy Isoflavone Extract Label, Solgar Laboratories, Leonia, NH 07605 (Date Unavailable).

Do Isoflavonoids From Soy Protein Have Proestrogenic Effects During the Menopausal Transition, Project #IOW03428; Agency: CSRS IOW, Iowa State University, Ames, Iowa 50011; Investigator: D.L. Alekel; Start Date: Sep. 16, 1996.

Flynn, M.E., *What's Hot and What's Not: EN's 1997 A–Z Guide to Nutrition*, Environmental Nutrition, 20:1, Jan. 1997, p. 1.

Chen, et al., *The 10 Greatest Medical Advances of 1996*, Health, 11:1, Jan.–Feb. 1997, p. 92.

Greenwood, S., *M.D. Shares Notes on Soy Symposium*, Menopause News, 6:6, Nov.–Dec. 1996, p. 1.

*Natural Progesterone and Soy on Menopause Agenda*, Menopause News, 6:6, Nov.–Dec. 1996, p. 1.

Andersen–Parrado, P., *Phytoestrogens Put Up a Strong Fight Against Memopause, Cancer*, Better Nutrition, 58:10, Oct. 1996, p. 20.

*Menopausal Symptoms Relieved with New Homeopathic Formula*, Better Nutrition, 58:2, Feb. 1996, p. 22.

McCord, H., *Savor the New White–hot Superfood*, Prevention 48:1, Jan. 1996, p. 79.

*Questions Raised and Results Reported at NAMS 6*, Menopause News, 5:5, Sep.–Oct. 1995, p. 3.

Perlmutter, C., *Triumph Over Menopause: Results From Our Exclusive Woman–to–Women Survey*, Prevention, 46:8, Aug. 1994, p. 78.

Greissinger, L., *9 Foods You Can Use As Medicine*, McCall's, 121:1, Oct. 1993, p. 38.

*Menopause Alters Dietary Needs*, Envrionmental Nutrition, 15:10, Oct. 1992, p. 7.

*Is Beanut Butter the Better Bet*, Environmental Nutrition, 20:4, Apr. 1997, p. 8.

*Humble Bean; Rich Benefits*, Vegetarian Times, No. 232, Dec. 1996, p. 20.

*The Benevolent Bean*, Better Homes & Gardens, 74:10, Oct. 1996, p. 76.

Bates, C.D., *Eating Well Through the Decades: Enjoy Optimal Nutrition at Every Age*, Vegetarian Times, No. 223, Mar. 1996, p. 66.

Jacobi, D., *The World's Healthiest Diet*, Natural Health, 26:1, Jan.–Feb. 1996, p. 90.

Harrigan, P., *Symposai: Examining the Benefits of Dietary Phytoestrogens*, Inpharma, Dec. 6, 1996.

Adlercreutz et al., *Letters to the Editor: Dietary Phyto–oestrogens and the Menopause in Japan*, The Lancet, 339:8803, May 16 1992, p. 1233.

McCord, H., *Menopause Naturally*, Prevention, 48:8, Aug. 1996, p. 65.

Somer, E., *Managing Menopause With Diet*, Better Homes and Gardens, 75:3, Mar. 1997, p. 102.

Baird et al., *Dietary Intervention Study to Assess Estrofenicity of Dietary Soy Among Postmenopausal Women*, J. Clin Endoerinol Metab 80, pp. 1685–1690, 1995.

Ferguson, L., *Consumer's Nutrition Attitudes and actions in US and Canada*, Food in Canada, 56:1, Jan.–Feb. 1996, p. 28.

*Preventing Breast Cancer*, Domestic News, San Frandisco, CA, Nov. 22, 1994.

Springer, I., *Foods That Keep You Young*, Weight Watchers Magazine, 29:6, Jun. 1996, p. 22.

*New Home Saliva Test Measures Hormones*, Menopause News, 6:2 pl(3), Mar.–Apr. 1996.

Adlercreutz et al,, *Determination of Urinary Lignans and Phytoestrogen Metabolites, Potential Antiestrogens and Anticarcinogens, in Urine of Women on Various Habitual Diets*, J. steroid Biochem, 25:5B, pp. 791–797, 1986.

Adlercreutz et al., *Urinary Excretion of Lignans and Isoflavonoid Phytoestrogens in Japanese Men and Women Consuming a Traditional Diet*, Am J Clin Nutr, 54:1093–1100, 1991.

Goldin et al., *The Relationship Between Estrogen Levels and Diets of Caucasian American and Oriental Immigrant Women*, Am J Clin Nutr, 44:945–53, 1986.

Rowland, I.R., *Role of the Gut Flora In Toxicity and Cancer*, Academic Press Limited, 1988.

Fugh–Berman, A., *Phytoestorogens*, Botanical Medicine in Modern Clinical Practice, 7 pp., May 16, 1996.

Messina et al., *Soyfacts: Soyfoods & Allergies*, No. 1–11 (No Date available).

Calabresi et al., *Chemotherapy of Neoplastic Diseases*, Goodman & Gilman, The Pharmacological Basis of Therapeutics, 6th Ed., Section XIII, 1980.

Stanton, et al., *Serum Magnesium in Women During Pregnancy* . . . , J Amer Coll Nutr., vol. 6, No. 4, pp. 313–319, 1987.

Wallach, S., *Effects of Magnesium on Skeletal Metabolism*, Magnesium Trace Elem, vol. 9, pp. 1–14, 1990.

Sandstead, et al., *Zinc Nutriture in The Elderly*, Amer J Clin Nutr, vol. 36, pp. 1046–1059, 1982.

Saltman, et al., *The Role of Trace Minerals in Osteoporosis*, J Amer Coll Nutr, vol. 12, pp. 384–389, 1993.

Bulpitt, C.J., *Vitamin C and Blood Pressure*, J Hypertension, vol. 8, pp. 1071–1075, 1990.

Block, G., *Epidemiologic Evidence Regarding Vitamin C and Cancer*, Am J Clin Nutr, vol. 54, pp. 1310S–1314S, 1991.

Anderson, et al., *Meta–Analysis of The Effects* . . . , Mew England J Med, vol. 333, No. 5, pp. 276–282, Aug. 3, 1995.

Carroll, *Review of Clinical Studies on* . . . , Perspectives in Practice, vol. 91, No. 7, pp. 820–827, Jul. 1991.

Potter, et al., *Depression of Plasma Cholesterol in Men*, Am J Clin Nutr, vol. 58, pp. 501–506, 1993.

Widhalm, et al., *Effect of Soy Protein Diet Versus* . . . , The J. Pediatr., vol. 123, No. 1, pp. 30–34, 1993.

Wynder, et al., *Nutrition and Prostate Cancer* . . . , Nutrition and Cancer, vol. 22, pp. 1–10, 1994.

Henley, et al., *Protein Quality Evaluation by Protein Digestibility*, Food Technology, pp. 74–77, Apr. 1994.

Young et al, *Evaluation of the Protein Quality* . . . , Am J Clin Nutr, Vol. 39, pp. 16–24, Jan. 1984.

Abstracts, The J of Nutr, First International Sympsm on the Role of Soy in Preventing and Treating Chronic Disease, vol. 125, No. 3S, pp. 799S–808S, Mar. 1995.

Speaker Abstracts, First International Sympsm on the Role of Soy in Preventing and Treating Chronic Disease, pp. 6–14, Feb. 1994.

Anderson, *Chromium, Glucose Tolerance, and Diabetes*, Biological Trace Element Research, vol. 32, pp. 19–24, 1992.

Wallach, *Clinical and Biochemical Aspects of Chromium Deficiency*, J of Amer Col of Nutrition, vol. 4, pp. 107–120, 1985.

Moorandian, et al., *Micronutrient Status in Diabetes Mellitus*[1,2], Am J Clin Nutr, vol. 45, pp. 877–895, 1987.

Mertz, *Chromium in Human Nutrition: A Review*, Amer Inst of Nutr, pp. 626–633, 1993.

DIETARY SUPPLEMENTS

This application is a continuation-in-part application of application Ser. No. 08/688,448 filed on Jul. 30, 1996, now U.S. Pat. No. 5,654,011.

FIELD OF THE INVENTION

The present invention relates to dietary supplements. More particularly, it relates to dietary supplements formulated to supplement a woman's specific micronutrient and phytochemical needs during each of her adult life stages, thereby promoting her well being and preventing or reducing the health risks to which she is exposed.

BACKGROUND OF THE INVENTION

The nutritional and health needs of women differ in many respects from those of men. Moreover, they vary with each developmental or life stage. For women, in particular, each adult life stage poses wide ranging nutritional requirements that significantly affect the health risks to which they are exposed.

In general, women pass through three principal adult developmental or life stages—the childbearing or pre-perimenopausal stage; the perimenopausal and menopausal stage; and the post-menopausal stage. Numerous health conditions and risks may develop during each of these life stages. They include coronary heart disease (CHD), some cancers, cervical dysplasia, menopause, osteoporosis, premenstrual syndrome (PMS), iron deficiency anemia, and fetal neural tube defects. The incidence of these conditions and risks varies with each life stage and has been shown to be influenced by diet and dietary supplements.

CHD is a major cause of death in women. It claims the lives of nearly 250,000 women per year, most of whom are post-menopausal. Although generally not manifest until the post-menopausal stage, CHD develops over decades. Well established risk factors for CHD include elevated plasma cholesterol levels and abnormal glucose metabolism. Also implicated in the development of CHD are elevated homocysteine levels and the effects of free radicals. Phytoestrogens, antioxidants, chromium and folic acid have been shown to mitigate these risk factors.

In general, the risk of cancer increases with age. Breast cancer, which afflicts one in every nine women, is chief among women's concerns. Both antioxidants and phytoestrogens appear to have a role in the prevention of some cancers, particularly breast cancer. Furthermore, folic acid has been shown to reduce the risk of cervical dysplasia, which is a precursor to cervical cancer.

Menopause can result in various unpleasant symptoms, including hot flashes, night sweats, mood swings, insomnia and fatigue. Phytoestrogens have been shown to reduce these symptoms.

Osteoporosis is associated with the aging process and predominantly affects women. It is characterized by diminished bone density, which results in increased bone fractures and vertebral column collapse. Bone loss begins around age 35. This loss accelerates during the menopause, which generally occurs around age 45 to 55. Osteoporosis develops over decades and is related to peak bone mass, as well as to the degree of bone loss. Adequate calcium intake prevents osteoporosis. Moreover, certain vitamins and minerals enhance calcium absorption and utilization.

PMS is a common recurring multi-symptom condition experienced by many menstruating women. Symptoms include water retention, breast tenderness, headaches, mood swings, etc. Vitamin $B_6$ has been shown to reduce some of these symptoms.

Iron deficiency anemia is also prevalent in women, particularly in menstruating women, but can also be found among elderly women. Treatment of iron-deficiency anemia generally consists of iron supplementation. Iron, however, is not readily absorbed and can cause constipation, particularly in the elderly. The presence of vitamin C in adequate amounts increases the bioavailability of iron.

Fetal neural tube defects may occur during the first month of gestation, often before a woman is aware of her pregnancy. Folic acid prevents fetal neural tube defects and, therefore, should be consumed in sufficient quantities by women of child-bearing age.

Preventive measures are probably the most effective method of dealing with these conditions and such measures should include diet and dietary supplementation. Although the etiology of disease is multi-factorial, certain dietary supplements have been shown to provide a statistically significant benefit in reducing the risk or reducing the incidence of various diseases and conditions. However, to date, the approach to micronutrient supplementation has not considered the changing needs of adult women. A more individualized, sophisticated, and targeted approach is clearly necessary. Because the incidence of these conditions varies with the different life stages of a woman, there is a need for dietary supplementation targeted to these changing health risks at each of the life stages.

SUMMARY OF THE INVENTION

In one aspect of the present invention there are provided dietary supplements for supplementing the dietary needs of women and preventing or reducing life stage associated health risks during each of their principal adult life stages (pre-perimenopause, perimenopause and menopause, or post-menopause).

In one embodiment of this aspect of the invention there is provided a dietary supplement for supplementing the micronutrient and phytochemical needs of pre-perimenopausal women to prevent or reduce the risk of fetal neural tube defects, iron deficiency anemia, PMS, osteoporosis, coronary heart disease, cervical dysplasia and some cancers throughout that stage and the rest of a woman's life, comprising about 200 to about 500 mg calcium, about 100 to about 200 mg magnesium, about 0.5 to about 1.5 mg boron, about 0.5 to about 1.5 mg copper, about 2 to about 2.6 mg manganese, about 10 to about 13 mg zinc, about 200 to about 300 IU vitamin D, about 12 to about 18 mg iron, about 400 to about 440 $\mu$g folic acid, about 2 to about 10 $\mu$g vitamin $B_{12}$, about 50 to about 100 mg vitamin $B_6$, about 50 to about 100 $\mu$g chromium, about 100 to about 200 IU vitamin E, about 100 to about 1000 mg vitamin C and about 8 to less than 50 mg phytoestrogen in admixture with a biologically acceptable carrier.

In another embodiment of this aspect of the invention the dietary supplement is formulated to supplement the changing nutritional needs of perimenopausal and menopausal women for the prevention or reduction of the risk of PMS, symptoms of menopause, fetal neural tube defects, osteoporosis, CHD, cervical dysplasia and some forms of cancer throughout that stage and the rest of a woman's life. This dietary supplement comprises from about 200 to about 1000 mg calcium; from about 100 to about 200 mg magnesium; from about 1.5 to about 2.5 mg boron; from about 1.5 to about 2.5 mg copper; from about 2.4 to about 3.6 mg manganese; from about 12 to about 15 mg zinc; from about 300 to about 400 IU vitamin D; from about 10 to about 15 mg iron; from about 400 to about 440 μg folic acid; from about 2 to about 15 μg vitamin $B_{12}$; from about 50 to about 100 mg vitamin $B_6$; from about 75 to about 200 μg chromium; from is about 200 to about 400 IU vitamin E; from about 200 to about 1000 mg vitamin C; and from about 10 to less than 50 mg phytoestrogen in admixture with a biologically acceptable carrier.

In yet another embodiment of this aspect of the invention the dietary supplement is formulated to supplement the increased nutritional needs of post-menopausal women for the prevention or reduction of the risk of coronary heart disease, some forms of cancer and osteoporosis throughout the final stage of her life. This dietary supplement comprises about 200 to about 1500 mg calcium, about 150 to about 250 mg magnesium, about 2.5 to about 3.5 mg boron, about 2.5 to about 3.5 mg copper, about 4.4 to about 5.6 mg manganese, about 15 to about 18 mg zinc, about 300 to about 800 IU vitamin D, about 5 to about 10 mg iron, about 400 to about 440 μg folic acid, about 2 to about 18 μg vitamin $B_{12}$, about 1.6 to about 10 mg vitamin $B_6$, about 100 to about 200 μg chromium, about 350 to about 800 IU vitamin E, about 300 to about 1000 mg vitamin C and about 10 to less than 50 mg phytoestrogen in admixture with a biologically acceptable carrier.

The dietary supplements of this invention may be formulated as a tablet, capsule, powder, gel or liquid, or dietary bar and are preferably formulated for once daily administration. They may be provided as a series or as individual compositions.

In another aspect of the invention, there is provided a method for supplementing the dietary needs and preventing or reducing life stage associated health risks in pre-perimenopausal women, perimenopausal and menopausal women, and/or post-menopausal women. This method comprises the administration to the woman of an effective amount of the life stage appropriate dietary supplement of the invention throughout that life stage. Preferably, a life stage appropriate dietary supplement of the invention is administered throughout each of the three principal adult life stages of the woman.

Unexpectedly, the compositions of the present invention provide women with physiologically effective phytoestrogen even when phytoestrogens are administered at levels of less than 25 mg per day, preferably at levels of less than 20 mg per day. As such, it is another advantage of this invention to provide compositions and methods for supplementing women's micronutrient needs by providing phytoestrogens at these levels.

In another aspect of the invention there is provided a once daily dietary supplement formulated specifically for the nutritional needs of peri-menopausal and menopausal women. This dietary supplement comprises less than about 20 mg phytoestrogen, preferably less than about 15 mg, and most preferably about 14.5 mg to about 1 mg phytoestrogen once a day in admixture with a biologically acceptable carrier.

There is further provided a method of supplementing the dietary needs of peri-menopausal and menopausal women. This method comprises administering a composition comprising less than 20 mg phytoestrogen, preferably less than about 15 mg and most preferably from less than about 14.5 mg to about 1 mg phytoestrogen once per day to a woman in need thereof in admixture with a biologically acceptable carrier.

DETAILED DESCRIPTION OF THE INVENTION

The present invention provides dietary supplements for women that are designed to meet a woman's health needs at each particular stage of her life, such as pre-perimenopause, perimenopause and menopause, or post-menopause, or during transition from one such life cycle into the next. This is accomplished by supplying, in the dietary supplements of the invention, a variety of nutrients that address common health risks associated with each of these life stages. Thus, each of the dietary supplements of the present invention provides a variety of nutrients, including antioxidants to increase the resistance of LDL cholesterol to oxidation, elements to enhance calcium absorption and utilization, nutrients to address iron deficiency anemia, folic acid to prevent fetal neural tube defects, compounds to reduce serum homocysteine and improve the lipid profile and phytoestrogens to reduce the symptoms of menopause, as well as to help in the prevention of osteoporosis, breast cancer and CHD. Furthermore, the amount of each nutrient present varies according to the life stage for which the composition is targeted.

The life stage specific dietary supplements of this invention are not meant to replace a well-balanced diet, but are instead intended to supplement a prudent diet. Unlike known broad-based dietary supplements, this invention does not merely provide the prescribed Recommended Daily Allowance (RDA) of micronutrients, but rather is geared to emphasize the disease prevention properties of micronutrient supplementation. Thus, cumulative beneficial and preventive effects should be achieved by dietary supplementation with the appropriate dietary supplement of the invention, especially when diligently used for more than one life stage.

As discussed above, a woman passes through three principal adult life stages. The onset of each of the various lifestages can occur at different ages for different individuals and the ages suggested below for the various lifestages are only approximations. The pre-perimenopause life stage (Stage I), approximately ages 18 to 45, includes the childbearing or reproductive life stage, which is a period of maximum ovarian function. Major health concerns that arise during this life stage include iron deficiency anemia, PMS and prevention of neural tube defects during pregnancy.

The perimenopause and menopause stage (Stage II), approximately ages 45 to 55, is characterized by decreasing ovarian function. At first, menstrual cycles may be erratic and PMS may intensify. For 80% of all women this stage will eventually include symptoms of the menopause, such as hot flashes, night sweats, insomnia, fatigue, and mood swings. The rate of bone loss accelerates and the lipid profile becomes more atherogenic, thus setting the stage for the future onset of CHD and osteoporosis.

The final stage, post-menopause (Stage III), age 55 plus, is characterized by complete cessation of ovarian function and an increase in the incidence of cancer, osteoporotic fracture and CHD. Menstrual related anemia, PMS and pregnancy are no longer health concerns during this life stage.

The dietary supplements of this invention contain vitamins, minerals and other compounds that are specifically included to address common health concerns that arise during each of these life stages. Moreover, they are formulated to prevent or lessen the risk of conditions known to develop in later life stages. For example, the dietary supplement intended for use during pre-perimenopause (Stage I dietary supplement) contains compounds to counter the risk of fetal neural tube defects, lessen or prevent PMS and iron deficiency anemia and prevent or lessen the risk of osteoporosis, coronary heart disease and cancer, which are generally manifest in the post-menopause life stage.

Phytoestrogens are included in each of the dietary supplements of this invention. These compounds have been demonstrated by clinical trials to modulate the menstrual cycle, reduce menopausal symptoms, and lower LDL cholesterol levels. J. Nutr., 1996, 126(1): 161–7; N. Engl. J. Med., 1995, 333: 276–82. Epidemiologic observations indicate women in countries where diets are rich in phytoestrogen (averaging about 40–50 mg/day) have a decreased incidence of breast cancer, menopausal symptoms and osteoporosis. Nutr. Cancer, 1994, 21:113–131; J. Nutr., 1995, 125; 757S–770S; Am. J. Clin. Nutr. 1995, 62:645. Animal studies have provided a biological basis for these observations. J. Ster. Biochem & Mol. Bio., 1992, 41(3–8): 331–7; First International Symposium on the role of Soy and Preventing and Treating Chronic Disease (1994), Speaker Abstracts.

In particular, with respect to alleviating menopausal symptoms, the use of moderate to high levels, i.e., generally from at least 20 to 90 mg per day of phytoestrogens, to reduce the symptoms of menopause is known in the art. Some researchers believe that a diet having such moderate to high levels of phytoestrogens may play a role in reducing the incidence of distressful symptoms of menopause; others believe that phytoestrogens alone are inadequate without adjunctive therapy. Adlercruetz, et al. INPHARMA (1996), *Examining the Benefits of Dietary Phytoestrogens;* Adlercruetz, et al., The Lancet (1992), 339:1233. Id. U.S. Pat. No. 5,498,631 discloses that moderate to high levels of isoflavonoids effectively reduce the symptoms of conditions caused by altered levels of estrogen such as menopause and premenstrual syndrome. Solgar, a New Jersey company, provides a pill called "Genistein" formulated from soy isoflavone extract containing 15 to 20 mg of a mixture of genestein and daidzein for twice daily consumption, which would provide at least 30 to 40 mg phytoestrogen per day.

Phytoestrogens are a class of isoflavones or isoflavonoids derived from plants, commonly soy beans. The plant source, however, is not critical. Some phytoestrogens, such as genistin, glycitin and diadzin contain a glycosidic moiety, whereas other phytoestrogens are nonglycosylated, e.g., genistein, glycitein and daidzein. Phytoestrogens obtained from a single plant generally are a mixture of both glycosylated and nonglycosylated forms. The present dietary supplements generally contain a mixture of phytoestrogens; however, purified phytoestrogens may be used. Mixtures of phytoestrogen may be obtained commercially. Phytoestrogen levels of less than 25 mg per day, preferably greater than 5 to about 25 mg per day, and most preferably about 10 to about 20 mg per day, provide women with phytoestrogen levels that are physiologically effective and may be used to supplement women's micronutrient needs.

Vitamin $B_{12}$, vitamin $B_6$ and folic acid are included in each of the life stage specific dietary supplements of this invention. These elements act synergistically to reduce serum homocysteine, high levels of which are associated with coronary heart disease. Am. J. Clin. Nutr., 1992, 55:131–138; New Eng. J. Med., 1992, 32:1832–1835; Am J. Clin. Nutr., 1989, 50:353–358. The amount of folic acid in the three dietary supplements of this invention is maintained at about the same level in all three compositions, since folic acid not only reduces the risk of fetal neural tube defects, but, as noted above, also has been shown to have beneficial cardiac effects and to decrease the risk of cervical dysplasia. Scand. J. Clin. Lab Invest., 1988, 48:215–221. On the other hand, larger doses of vitamin $B_6$ are included in the Stage I and Stage II formulations, as compared to Stage III, to assist in alleviating PMS symptoms. J. Royal Coll. Gen. Prac., 1989, 39:364–368; Obstetrics and Gyn., 1987, 70:147–149.

Other components of the dietary supplements of this invention include vitamin D, calcium, magnesium, manganese, copper, zinc, boron and chromium. The combination of vitamin D, and magnesium, manganese, copper, zinc, and boron (the "enhancement compounds") acts synergistically with calcium to improve calcium absorption and/or utilization and thereby enhance bone density. Am. J. Clin. Nutr., 1982, 36:1046–1059; J. Am Col. Nutr., 1993, 12:383–389; Magnesium Trace Elem., 1990, 9:61–69; Am. J. Clin. Nutr., 1991, 54:177S–226S; Clin. Obstetrics and Gyn., 1987, 30:789–811. Chromium is included to optimize glucose and lipid metabolism. Diabetes Care, 1994, 17:1449–1452; Metabolism, 1992, 41:768–771; Biol. Trace Element Res., 1992, 32:19–24.

Aging is associated with an increased production of oxygen free radicals (highly toxic molecules) which contribute to the pathogenesis of many chronic diseases. This invention is formulated to address this issue. Thus, antioxidants, such as vitamin E, are included particularly to reduce atherogenicity of LDL cholesterol particles which reduces damage to arterial walls. Am. J. Clin. Nutr., 1991, 53:305S–313S; Lancet, 1996, 347:781–786. Another antioxidant, Vitamin C, is included to lower the risk of breast and other cancers. Vitamin E and Vitamin C may work together in a synergistic fashion. Am. J. Clin. Nutr. 1991, 54: 1310S–1314S.

Each of the life stage dietary supplements of this invention are formulated specifically to contain an amount of each of the above-discussed components sufficient to prevent or reduce health risks associated with Stage I, Stage II or Stage III of a woman's life.

The dose of iron is highest in the Stage I dietary supplement of this invention and lowest in the Stage III dietary supplement, because iron deficiency anemia is a major health concern of menstruating women (Stage I and part of Stage II). Vitamin $B_{12}$ deficiency results in pernicious anemia. Because this condition can be clinically masked if folate is provided in the diet without vitamin $B_{12}$, all formulations of this invention contain both folic acid and Vitamin $B_{12}$.

Stage I compositions also contain an amount of vitamin $B_6$ sufficient to reduce symptoms of PMS and to compensate for reduced levels of this vitamin caused by oral contraceptive use. The amount of folic acid contained in the Stage I nutritional supplement is sufficient to prevent fetal neural tube defects during pregnancy, as well as to reduce the risk of cardiovascular disease by maintaining low homocysteine levels. It also reduces the risk of cervical dysplasia.

Thus, the Stage I dietary supplement contains an amount of vitamin $B_6$ sufficient to reduce the effects of PMS, an amount of folic acid sufficient to prevent fetal neural tube defects and provide cardiac benefit, a sufficient amount of vitamin $B_{12}$ to act in concert with vitamin $B_6$ and folic acid present in the composition to reduce the levels of serum homocysteine, a sufficient amount of chromium to enhance glucose and lipid metabolism, antioxidants to help prevent CHD and some cancers, and calcium, together with a combination of other nutrients known to enhance its absorption and/or utilization to prevent osteoporosis, and an amount of phytoestrogens to beneficially modulate menses and provide protection against osteoporosis, some cancers and CHD. The Stage I dietary supplement is therefore particularly suited to meet the needs and address the health risks of a young adult female, while also lessening the risk of osteoporosis, cancer and coronary heart disease occurring in later life.

The dietary supplements formulated for the perimenopause and menopause lifestage (Stage II composition) include a higher dosage of phytoestrogens than used in the dietary supplement for the pre-perimenopausal lifestage because phytoestrogens reduce menopausal symptoms, and to provide even more protection against osteoporosis, cancer and CHD, the incidence of all of which increases with age. Similarly, components that affect calcium uptake and utilization are also increased in the Stage II dietary supplement since the amount of bone loss increases with menopause.

Concomitant with the onset of the menopause is a worsening of the lipid profile. LDL-cholesterol and total cholesterol increase significantly, while HDL-cholesterol decreases. To address this problem, the levels of both phytoestrogens and chromium have been increased in the Stage II composition relative to the Stage I composition. Antioxidant levels have also been increased to help prevent the age-related onset of CHD and breast cancer.

The Stage III dietary supplement of this invention is formulated to address the health concerns and health risks that occur with greater frequency in the post-menopausal years, e.g., osteoporosis, cancer and coronary heart disease. Stage III compositions contain phytoestrogen in the same concentration as Stage II. However, calcium, vitamin D, and the enhancement compounds are increased, as are the antioxidants and chromium. Chromium has a positive effect on blood sugar levels and the lipid profile. On the other hand, the levels of vitamin $B_6$ and iron are decreased, because the health concerns addressed by higher amounts of these components are of less relevance.

Optionally, the dietary supplements of this invention may further contain an amount of vitamin A or mixed carotenoids sufficient to supplement the nutritional needs of a woman at a particular lifestage. Vitamin A may be provided as preformed vitamin A or as mixed carotenoids, or both. There are more than 500 naturally occurring carotenoids, about 50 of which can serve as precursors of retinol and therefore have provitamin A activity. These include alpha- and beta-carotene and cryptoxanthin. However, non provitamin A carotenoids, such as lutein and lycopene have also been shown to have beneficial effects and may also be provided. Lycopene intake, for example, has been inversely associated with the risk of cervical cancer. Nutr & Cancer 1994, 21:193–201; Internat J. Cancer 1991; 48:34–8.

The amount of preformed vitamin A and mixed carotenoids included in the Stage I dietary supplement is in the range of about 400 to about 1200 μg RE, preferably about 600 to about 1000 μg RE, and most preferably about 800 μg RE. The amount of preformed vitamin A and mixed carotenoids included in the Stage II dietary supplement is in the range of about 800 to about 1600 μg RE, preferably about 1000 to about 1400 μg RE, and most preferably about 1200 μg RE. The amount of preformed vitamin A and mixed carotenoids included in the Stage III dietary supplement is in the range of about 1200 to about 2000 μg RE, preferably about 1400 to about 1800 μg RE, and most preferably about 1600 μg RE. Preferably, the amount of preformed vitamin A is about 200 to about 400 μg RE, and most preferably about 400 μg RE.

Each of the dietary supplements of this invention is formulated to prevent and reduce the risk of disease during one of three specific life stages, during the transition from one life stage to the next, and during later stages of life. Administration of the dietary supplements of this invention during the appropriate life stage reduces the risk factors for disease, such as iron deficiency anemia during the pre-perimenopausal life stage, high cholesterol during the peri-menopausal and menopausal life stage, and CHD, osteoporosis, and some cancers during the post-menopausal life stage.

Maximum benefit is obtained by supplementation of the diet with the life stage appropriate dietary supplement throughout the entire life cycle; however, benefit is also obtained when supplementation is begun at any time during a particular life cycle.

For example, supplementation of the diet with the Stage I dietary supplement at age 30 to 40, which is well into the pre-perimenopausal life stage, lowers the risk of, or prevents, future osteoporosis, cancer and coronary heart disease, and provides health benefits to those conditions that present during this life cycle, e.g., PMS, fetal neural tube defects, and iron deficiency anemia. It is understood that the phrase "administration throughout the life cycle", as used herein, means continual administration from any time during a life cycle that supplementation is begun.

The dietary supplements of the present invention may be formulated using any pharmaceutically acceptable forms of the vitamins, minerals and other nutrients discussed above, including their salts. Preferred forms are calcium carbonate, magnesium hydroxide or magnesium sulfate, sodium tetraborate, cupric oxide, manganese sulfate, zinc sulfate, cholecalciferol, ferrous fumarate, pyridoxine hydrochloride, chromium picolinate, d-alpha-tocopherol acetate, and ascorbic acid. They may be formulated into capsules, tablets, powders, gels or liquids. The dietary supplements may be formulated as powders, for example, for mixing with consumable liquids such as milk, juice, water or consumable gels or syrups for mixing into other dietary liquids or foods. The dietary supplements of this invention may be formulated with other foods or liquids to provide premeasured supplemental foods, such as single serving bars, for example. Flavorings, binders, protein, complex carbohydrates, and the like may be added as needed.

The dietary supplements of the invention are intended for daily administration. Preferably, they are formulated for once-daily administration, but may be formulated in multiple portions or as time release compositions for more or less frequent administration; for example, the dietary supplement may be formulated as two tablets for twice daily administration, or as a sustained release capsule for administration every three days. In the latter instance, the capsule is formulated to release the daily amount of nutrients prescribed by the dietary supplements of the invention during each of the three days. For reasons of size (ease of swallowing) or improved bioabsorption or utilization (e.g., before or after a meal or before sleep), a given dosage may be divided into two, three, or more tablets (or capsules, etc.). A daily dosage may be administered as one tablet, as two tablets taken together, or as two tablets taken separately (e.g., one in the morning and one in the evening).

Specific formulation for each of the three lifestage specific dietary supplements is provided below.

STAGE I DIETARY SUPPLEMENT

The dietary supplement for pre-perimenopausal women includes from about 200 to about 500 mg calcium, preferably from about 200 to about 300 mg calcium, and most preferably about 200 mg calcium; from about 100 to about 200 mg magnesium, preferably from about 100 to about 150 mg magnesium, and most preferably about 100 mg magnesium; from about 0.5 to about 1.5 mg boron, preferably about 0.7 to about 1.3 mg boron, and most preferably about 1 mg boron; from about 0.5 to about 1.5 mg copper, preferably about 0.7 to about 1.3 mg copper, and most preferably about 1 mg copper; from about 2 to about 2.6 mg manganese, preferably about 2 to about 2.4 mg manganese, and most preferably about 2 mg manganese; from about 10 to about 13 mg zinc, preferably about 10 to about 12 mg zinc, and most preferably about 10 mg zinc; from about 200 to about 300 IU vitamin D, preferably about 200 to about 250 IU vitamin D, and most preferably about 200 IU vitamin D; from about 12 to about 18 mg iron, preferably about 16 to about 18 mg iron, and most preferably about 18 mg iron; from about 400 to about 440 µg folic acid, preferably about 400 to about 420 µg folic acid, and most preferably about 400 µg folic acid; from about 2 to about 10 µg vitamin $B_{12}$, preferably about 2 to about 4 µg vitamin $B_{12}$, and most preferably about 2 µg vitamin $B_{12}$; from about 50 to about 100 mg vitamin $B_6$, preferably about 50 to about 65 mg vitamin $B_6$, and most preferably about 50 mg vitamin $B_6$; from about 50 to about 100 µg chromium, preferably about 50 to about 75 µg chromium, and most preferably about 50 µg chromium; from about 100 to about 200 IU vitamin E, preferably about 100 to about 150 IU vitamin E, and most preferably about 100 IU vitamin E; from about 100 to about 1000 mg vitamin C, preferably about 100 to about 150 mg vitamin C, and most preferably about 100 mg vitamin C; and from about 8 to less than 50 mg phytoestrogen, preferably about 8 to about 12 mg phytoestrogen, and most preferably about 10 mg phytoestrogen.

This range of folic acid has been shown to be effective in preventing fetal neural tube defects and reducing the risk of cervical dysplasia; the amount of vitamin $B_6$ is sufficient to reduce at least some symptoms of PMS; the amounts of vitamin $B_{12}$, vitamin $B_6$ and folic acid have been shown to reduce serum homocysteine; the amount of iron present in the composition is sufficient to reduce or prevent iron deficiency anemia; and phytoestrogen, antioxidants and chromium help reduce the risk of cardiovascular disease. Antioxidants and phytoestrogens also provide some protection against osteoporosis and some cancers.

A preferred Stage I daily dietary supplement is shown in Table I.

STAGE II DIETARY SUPPLEMENT

The dietary supplement for perimenopausal and menopausal women includes from about 200 to about 1000 mg calcium, preferably from about 300 to about 400 mg calcium, and most preferably about 300 mg calcium; from about 100 to about 200 mg magnesium, preferably from about 100 to about 150 mg magnesium, and most preferably about 150 mg magnesium; from about 1.5 to about 2.5 mg boron, preferably about 1.7 to about 2.3 mg boron, and most preferably about 2 mg boron; from about 1.5 to about 2.5 mg copper, preferably about 1.7 to about 2.3 mg copper, and most preferably about 2 mg copper; from about 2.4 to about 3.6 mg manganese, preferably about 2.6 to about 3.4 mg manganese, and most preferably about 3 mg manganese; from about 12 to about 15 mg zinc, preferably about 12 to about 14 mg zinc, and most preferably about 12 mg zinc; from about 300 to about 400 IU vitamin D, preferably about 300 to about 350 IU vitamin D, and most preferably about 300 IU vitamin D; from about 10 to about 15 mg iron, preferably about 13 to 15 mg iron, and most preferably about 15 mg iron; from about 400 to about 440 µg folic acid, preferably about 400 to about 420 µg folic acid, and most preferably about 400 µg folic acid; from about 2 to about 15 µg vitamin $B_{12}$, preferably about 2 to about 6 µg vitamin $B_{12}$, and most preferably about 2 µg $B_{12}$; from about 50 to about 100 mg vitamin $B_6$, preferably about 50 to about 65 mg vitamin $B_6$, and most preferably about 50 mg vitamin $B_6$; from about 75 to about 200 µg chromium, preferably about 75 to about 100 µg chromium, and most preferably about 75 µg chromium; from about 200 to about 400 IU vitamin E, preferably about 200 to about 300 IU vitamin E, and most preferably about 200 IU vitamin E; from about 200 to about 1000 mg vitamin C, preferably about 200 to about 300 mg vitamin C, and most preferably about 200 mg Vitamin C; and from about 10 to less than 50 mg phytoestrogen, preferably about 12 to about 17 mg phytoestrogen, and most preferably 15 mg phytoestrogen.

The amount of calcium, magnesium, boron, copper, manganese, zinc and vitamin D in the Stage II composition has been increased in comparison to the Stage I composition since these nutrients have been shown to enhance calcium absorption and/or utilization; the amount of vitamin $B_6$ is the same as in the Stage I composition and is sufficient to prevent or reduce symptoms of PMS; the amounts of folic acid will prevent fetal neural tube defects and reduce the risk of cervical dysplasia, and in combination with vitamin $B_{12}$ and vitamin $B_6$ is associated with a reduced risk of CHD; chromium has also been increased to help regulate the lipid profile and thereby reduce the risk of CHD; the amount of phytoestrogen contributes to the reduction of menopausal symptoms, osteoporosis, CHD and some forms of cancer, and therefore is increased in the composition for the second life stage. Similarly, the amount of antioxidants are increased in the Stage II composition because they also provide protection against CHD and some cancers.

A preferred Stage II daily dietary supplement is shown in Table I.

STAGE III DIETARY SUPPLEMENT

The dietary supplement for post-menopausal women includes from about 200 to about 1500 mg calcium, preferably from about 300 to about 500 mg calcium, and most preferably about 400 mg calcium; from about 150 to about 250 mg magnesium, preferably from about 150 to about 200 mg magnesium, and most preferably about 200 mg magnesium; from about 2.5 to about 3.5 mg boron, preferably about 2.7 to about 3.3 mg boron, and most preferably about 3 mg boron; from about 2.5 to about 3.5 mg copper, preferably about 2.7 to about 3.3 mg copper, and most preferably about 3 mg copper; from about 4.4 to about 5.6 mg manganese, preferably about 4.6 to about 5.4 mg manganese, and most preferably about 5.0 mg manganese; from about 15 to about 18 mg zinc, preferably about 15 to about 17 mg zinc, and most preferably about 15 mg zinc; from about 300 to about 800 IU vitamin D, preferably about 350 to about 400 IU vitamin D, and most preferably about 400 IU vitamin D; from about 5 to about 10 mg iron, preferably about 8 to 10 mg iron, and most preferably about 10 mg iron; from about 400 to about 440 µg folic acid, preferably about 400 to about 420 µg folic acid, and most preferably about 400 µg folic acid; from about 2 to about 18 µg vitamin $B_{12}$, preferably about 2 to about 8 µg vitamin $B_{12}$, and most preferably about 2 µg vitamin $B_{12}$; from about 1.6 to about 10 mg vitamin $B_6$, preferably about 1.6 to 3.2 mg vitamin $B_6$, most preferably about 1.6 mg vitamin $B_6$; from about 100 to about 200 µg chromium, preferably about 100 to about 150 µg chromium, and most preferably about 100 μg chromium; from about 350 to about 800 IU vitamin E, preferably about 350 to about 450 IU vitamin E, and most preferably about 400 IU vitamin E; from about 300 to about 1000 mg vitamin C, preferably about 350 to about 450 mg vitamin C, and most preferably about 400 mg vitamin C; and from about 10 to less than 50 mg phytoestrogen, preferably about 12 to about 17 mg phytoestrogen, and most preferably about 15 mg phytoestrogen.

The amounts of calcium, manganese, boron, copper, magnesium, zinc and vitamin D are optimized to enhance calcium uptake and/or utilization for the prevention of osteoporotic fractures; the amounts of antioxidant, vitamin $B_{12}$, vitamin $B_6$, folic acid, and chromium are maximized to prevent or reduce the risk of CHD; phytoestrogens and antioxidants contribute to reducing the risk of cardiovascular disease and some cancers.

A preferred Stage III daily dietary supplement is shown in Table I.

TABLE I

DIETARY SUPPLEMENTS

| COMPONENT | STAGE I | STAGE II | STAGE III |
| --- | --- | --- | --- |
| Calcium | 200 mg | 300 mg | 400 mg |
| Magnesium | 100 mg | 150 mg | 200 mg |
| Boron | 1 mg | 2 mg | 3 mg |
| Copper | 1 mg | 2 mg | 3 mg |
| Manganese | 2 mg | 3 mg | 5 mg |
| Zinc | 10 mg | 12 mg | 15 mg |
| Vitamin D | 200 IU | 300 IU | 400 IU |
| Iron | 18 mg | 15 mg | 10 mg |
| Folic Acid | 400 μg | 400 μg | 400 μg |
| Vitamin B12 | 2 μg | 2 μg | 2 μg |
| Vitamin B6 | 50 mg | 50 mg | 1.6 mg |
| Chromium | 50 μg | 75 μg | 100 μg |
| Vitamin E | 100 IU | 200 IU | 400 IU |
| Vitamin C | 100 mg | 200 mg | 400 mg |
| Phytoestrogen | 10 mg | 15 mg | 15 mg |

In a second aspect of the invention there is provided a method for preventing or lessening the risk of life stage associated diseases and health conditions in women by orally administering a dietary supplement of this invention during the appropriate life stage of the woman. For example, the Stage I dietary supplement of this invention is orally administered to a pre-perimenopausal woman, the Stage II dietary supplement is orally administered to the woman when she reaches the perimenopausal and menopausal stage and the Stage III dietary supplement of this invention is administered to the woman when she reaches the post-menopausal stage. In a preferred embodiment, the appropriate dietary supplement is administered throughout at least one life stage of the woman, most preferably throughout the three adult life stages defined herein.

Although approximate age ranges for these stages are noted above, any individual woman may have an accelerated course through these phases. Delayed transitions can also occur but are less likely. Thus, a woman taking the Stage I formulation who begins to experience hot flashes, insomnia, or other menopausal symptoms would benefit more from the Stage II formulation and should switch to that formulation at whatever age those symptoms occur. It is suggested that she remain on the Stage II formulation until she is clearly post-menopausal as determined by medical convention (generally an increased FSH—follicle stimulating hormone—and no menstrual cycle for twelve months). The Stage III formulation is then recommended.

Similarly, when a woman has had cessation of menses related to decreased ovarian function as determined by medical convention, she should switch from the Stage I to the Stage II formulation for at least six months to one year, even though she has had no distressing menopausal symptoms. When clearly through this transition phase, the Stage III formulation is recommended due to its additional preventive properties for post-menopausal diseases.

And, a woman who undergoes surgical menopause at an early age, e.g., at 35 years, no longer requires the Stage I formulation. While the Stage II composition would not be inappropriate for a year or two, the preferred formulation for this woman would be the Stage III formulation because she has gone from a child-bearing phase to a post-menopausal phase without a significant transition period.

The present method for preventing or lessening the risk of life stage associated health conditions is effective in the prevention of fetal neural tube defects, prevention or reduction of symptoms of PMS and menopause, prevention or reduction of the risk of developing osteoporosis, iron deficiency anemia, coronary heart disease, some cancers and cervical dysplasia.

In another aspect of the invention, there is provided a dietary supplement formulated specifically for perimenopausal and menopausal women. The supplement may also be used by pre-perimenopausal women to, for example, enhance the effects of supplementation once the perimenopausal and menopausal life stage is reached, or by post-menopausal women exhibiting residual symptoms of menopause. Use during the pre-perimenopausal life stages may also aid in regulating or may otherwise positively impact the menstrual cycle.

The dietary supplement of this aspect of the invention is a once daily supplement comprising physiologically effective phytoestrogen in an amount of less than about 20 mg, preferably less than about 15 mg and more preferably, less than about 14.5 mg to about 1 mg.

The phytoestrogen to be used may be selected from concentrated naturally-occurring phytoestrogen (such as whole soybean extract), synthesized phytoestrogen, or mixtures thereof. One or more different phytoestrogens may be included. Preferably, the phytoestrogen is selected from the group consisting of genistin, glycitin, daidzin, malonyl daidzin, malonyl genistin, malonyl glycitin, acetyl glycitin, acetyl daidzin, acetyl genistin, genistein, glycitein, daidzein and mixtures thereof.

The phytoestrogen may be derived from any suitable source, for example, from a plant extract rich in phytoestrogens. Preferably, the phytoestrogen is derived from whole soybean (as opposed to soy germ). Other sources of phytoestrogen however may be utilized. The phytoestrogens may be glycosylated, such as genistin, glycitin or daidzin, malonyl daidzin, malonyl genistin, malonyl glycitin, acetyl glycitin, acetyl daidzin, acetyl genistin, or non-glycosylated, such as genistein, glycitein or daidzein. Preferably, the phytoestrogen has the following phytoestrogen profile (by weight percent): about 31 to 35% daidzin, about 8 to 10% glycitin, about 36 to 40% genistin, about 3 to 5% malonyl daidzin, about 0.5 to 2.5% malonyl glycitin, about 2.6 to 4.6% malonyl genistin, about 3.7 to 5.7% acetyl daidzin, about 0.1 to 1.1% acetyl glycitin, about 3.2 to 5.2% acetyl genistin, about 0.1 to 1% daidzein, about 0.1 to 1% glycitein, and about 0.1 to 0.9% genistein. Most preferably the phytoestrogen has a phytoestrogen profile similar to that described in Table II, which sets forth the phytoestrogen profile for total phytoestrogens in a phytoestrogen concentrate derived from whole soybean.

The dietary supplement may be provided in tablet, patch, gel, cream or capsule form, for example or formulated in a palatable confection such as a confectionary bar, beverage, cereal, powder, chewing gum and the like.

In a preferred embodiment, there is provided a once daily dietary supplement containing a mixture of daidzin, glycitin, genistin, malonyl daidzin, malonyl genistin, malonyl glycitin, acetyl glycitin, acetyl daidzin, acetyl genistin, genistein, glycitein and daidzein in a total weight amount of about 10 to about 15 mg, more preferably 13 to 15 mg. Preferably, each of the phytoestrogens is provided in the following percentages (by weight) of the total phytoestrogens: about 33% daidzin, about about 9% glycitin, about 38% genistin, about 4% malonyl daidzin, about 1.5% malonyl glycitin, about 3.6% malonyl genistin, about 4.7% acetyl daidzin, about 0.6% acetyl glycitin, about 4.2% acetyl genistin, about 0.5% daidzein, about 0.5% glycitein, and about 0.4% genistein.

In a most preferred embodiment, a supplement is provided using about 50 mg of soybean phytoestrogen concentrate having the phytoestrogen profile set forth in Table II, to give a phytoestrogen content of 14.15. This tablet provides phytoestrogens in the following forms and amounts: about 4.726 mg daidzin, about 1.257 mg glycitin, about 5.312 mg genistin, about 0.586 mg malonyl daidzin, about 0.217 mg malonyl glycitin, about 0.510 mg malonyl genistin, about 0.670 mg acetyl daidzin, about 0.082 mg acetyl glycitin, about 0.595 mg acetyl genistin, about 0.076 mg daidzein, about 0.062 mg glycitein, and about 0.060 mg genistein (See Table II).

TABLE II

PHYTOESTROGEN SUPPLEMENT

| PHYTOESTROGEN | wt % | mg/50 mg of whole soybean phytoestrogen concentrate | ppm ($\mu$g/g) in whole soybean phytoestrogen concentrate |
|---|---|---|---|
| Daidzin | 33 | 4.726 | 94527 |
| Glycitin | 9 | 1.257 | 25144 |
| Genistin | 38 | 5.312 | 106239 |
| Malonyl Daidzin | 4 | 0.586 | 11721 |
| Malonyl Glycitin | 1.5 | 0.217 | 4341 |
| Malonyl Genistin | 3.6 | 0.510 | 10200 |
| Acetyl Daidzin | 4.7 | 0.670 | 13390 |
| Acetyl Glycitin | 0.6 | 0.082 | 1633 |
| Acetyl Genistin | 4.2 | 0.595 | 11907 |
| Daidzein | 0.5 | 0.076 | 1510 |
| Glycitein | 0.5 | 0.062 | 1243 |
| Genistein | 0.4 | 0.060 | 1192 |
| TOTAL | 100 | 14.15 | 283047 |

EXAMPLE 1

The diet of a pre-perimenopausal woman is supplemented daily with the Stage I dietary supplement of this invention. The dietary supplement is administered in tablet form formulated for once daily administration. Supplementation of the diet is carried out throughout the entire pre-perimenopausal life stage.

When the woman reaches the perimenopausal life stage, dietary supplementation is changed from the Stage I to Stage II dietary supplement of the invention. The Stage II dietary supplement is administered in the same manner as is the Stage I supplement. Dietary supplementation continues throughout perimenopause and menopause, after which the Stage III dietary supplement is administered in place of the Stage II supplement.

EXAMPLE 2

The diet of two menopausal women who were unable or unwilling to take hormonal replacement therapy (HRT) and who presented with menopausal symptoms including hot flashes, insomnia and night sweats that were marked to severe in quantity and/or quality was supplemented with a dietary regimen of about 15 mg/day phytoestrogen. Both women had been on HRT in the past (one woman for two and one half months and the other for two years). However, neither woman would consider its continued use. Both women had also tried alternative treatment regimens, such as acupuncture and Chinese herbs with little or no lasting relief.

Both women reported immediate relief (within several days) upon taking tablets containing about 15 mg/day of phytoestrogen. The effect got progressively better for four to six weeks at which time a plateau was reached. Each woman reported a significant reduction in hot flashes, i.e., from more than twenty per day to less than five per day, as well as a reduction in their intensity (from "hot" to "warm flushes"). Night sweats were also significantly reduced and both the duration and quality of sleep improved.

A SMAC-18 laboratory analysis was obtained for each woman prior to the start of phytoestrogen therapy and again at four to six weeks and at eight to thirteen weeks after onset of phytoestrogen therapy. There were no adverse changes in the SMAC-18 data. Specifically, kidney function and liver enzyme levels remained unchanged.

As a comparison, at least one of the women was provided with a phytoestrogen supplement already on the market to substitute for the phytoestrogen supplement of the invention. She reported that it was completely unsatisfactory.

What is claimed is:

1. A method of supplementing the dietary needs of a peri-menopausal and/or menopausal woman said method comprising administering to the woman a dietary supplementing amount of phytoestrogen per day, said dietary supplementing amount being less than 20 mg.

2. The method of claim 1 wherein the amount of phytoestrogen administered is less than about 15 mg per day.

3. The method of claim 1 wherein the phytoestrogen is selected from the group consisting of genistin, glycitin, daidzin, malonyl daidzin, malonyl genistin, malonyl glycitin, acetyl glycitin, acetyl daidzin, acetyl genistin, genistein, glycitein, daidzein and mixtures thereof.

4. The method of claim 1 wherein the phytoestrogen is obtained from whole soybean extract.

5. The method of claim 1 wherein the phytoestrogen comprises about 4.726 mg daidzin, about 1.257 mg glycitin, about 5.312 mg genistin, about 0.586 mg malonyl daidzin, about 0.217 mg malonyl glycitin, about 0.510 mg malonyl genistin, about 0.670 mg acetyl daidzin, about 0.082 mg acetyl glycitin, about 0.595 mg acetyl genistin, about 0.076 mg daidzein, about 0.062 mg glycitein, and about 0.060 mg genistein.

6. The method of claim 1 wherein the phytoestrogen comprises about about 31 to 35 wt % daidzin, about 8 to 10 wt % glycitin, about 36 to 40 wt % genistin, about 3 to 5 wt % malonyl daidzin, about 0.5 to 2.5 wt % malonyl glycitin, about 2.6 to 4.6 wt % malonyl genistin, about 3.7 to 5.7 wt % acetyl daidzin, about 0.1 to 1.1 wt % acetyl glycitin, about 3.2 to 5.2 wt % acetyl genistin, about 0.1 to 1.0 wt % daidzein, about 0.1 to 1.0 wt % glycitein, and about 0.1 to 0.9 wt % genistein.

* * * * *